United States Patent
Plunkett

(10) Patent No.: US 6,215,003 B1
(45) Date of Patent: Apr. 10, 2001

(54) SYNTHESIS OF ETHYLENEIMINE DIMER

(75) Inventor: Kevin S. Plunkett, Walpole, MA (US)

(73) Assignee: V.I. Technologies, Inc., Melville, NY (US)

( * ) Notice: Subject to any disclaimer, the term of this patent is extended or adjusted under 35 U.S.C. 154(b) by 0 days.

(21) Appl. No.: 09/493,544

(22) Filed: Jan. 28, 2000

Related U.S. Application Data

(60) Provisional application No. 60/117,789, filed on Jan. 29, 1999.

(51) Int. Cl.$^7$ .................................................... C07C 403/04
(52) U.S. Cl. ............................................. 548/962; 548/967
(58) Field of Search ............................................. 548/962

(56) References Cited

U.S. PATENT DOCUMENTS 3,502,654 * 3/1970 Young .................................. 548/967

OTHER PUBLICATIONS

Database Caplus on STN, Acc. No. 1971:510181, Young, 'Alkylenimine dimers.' DE 1965477 A (abstract).*
Database Caplus on STN, Acc. No. 1978:22490. Kanabus–Kaminska et al., 'Formation and separation of biaziridine and byproducts in the condensation fo N–chloro– and N–lithioaziridene.' Rocz. Chem. (1977), 51(6), p. 1253–7 (abstract).*
Borisenko et al., "Kinetics and mechanism of the intramolecular cyclization of 2–chloroethylethylenediamine," *Zhurnal Obshchei Khimii*, 55:1141–1146 (1985).
Chechik et al., "Regiochemistry and kinetics of cyclization of N–(2–chloroethyl) polyethylenepolyamines," *Zhurnal Obshchei Khimii*, 61:1676–1679 (1991).
Chechik et al., "Competition between three–membered–ring formation and intermolecular substitution: solvent effect," *J. Chem. Research* 256–257 (1994).
Jones et al., "The polymerization of ethylenimine," *J. Org. Chem.*, 9:125–147 (1944).
Kelly et al., "Cyclodehydration of N– and C–substituted β amino alcohols to the corresponding aziridines with diethoxytriphenylphosphorane," *J. Org. Chem.* 51:95–97 (1986).
Kostyanovskii et al., "Oligomer of Aziridines and N–β–Aziridinoethylamides," *Institute of Chemical Physics of the Academy of Sciences of the U,S,S,R, Moscow.* Translated from *Izvestiya Akademii Nauk SSSR, Seriya Khimicheskaya* 11:2566–2575 (1988).

* cited by examiner

*Primary Examiner*—Johann Richter
*Assistant Examiner*—Brian J. Davis
(74) *Attorney, Agent, or Firm*—Clark & Elbing, LLP; Paul T. Clark

(57) ABSTRACT

This invention provides a method for synthesizing ethyleneimine dimer which includes reacting 2-(2-aminoethylamino) ethanol with an aqueous HX solution to produce N-(2-haloethyl)-1,2-ethanediamine dihydrohalide; reacting this product with a base in a solvent to convert the N-(2-haloethyl)-1,2-ethanediamine dihydrohalide into ethyleneimine dimer; and purifying the dimer from the solvent. This method of synthesis provides several advantages over previous methods: (1) The starting compounds are all relatively inexpensive; (2) the yield of the product is greater than 20% of the theoretical yield; and (3) the steps of the synthesis are easy, inexpensive and amenable to large-scale production. All of these advantages allow for less expensive production of ethyleneimine dimer.

21 Claims, No Drawings

SYNTHESIS OF ETHYLENEIMINE DIMER

CROSS-REFERENCE TO RELATED APPLICATIONS

This application claims priority from U.S. Provisional Application Ser. No. 60/117,789, filed Jan. 29, 1999.

BACKGROUND OF THE INVENTION

The invention relates to methods for synthesizing compounds for the selective modification of nucleic acids in biological compositions.

The transmission of viral diseases (e.g., hepatitis A, B, and C, acquired immunodeficiency syndrome, and cytomegalovirus infections) by blood or blood products is a significant problem in medicine. Other biological compositions, such as mammalian and hybridoma cell lines, products of cell lines, milk, colostrum, and sperm, can also contain infectious viruses. Screening donor biological compositions for viral markers can help reduce the transmission of viruses to recipients, but many screening methods are directed to only a few discrete viruses, and are therefore incomplete, and may also be less than 100% sensitive. It is therefore important to inactivate viruses contained in donor blood, blood products, or other biological compositions.

A number of agents that are capable of inactivating viruses in blood have been developed. For example, ethyleneimine monomer and ethyleneimine oligomers (including dimers, trimers, and tetramers) are very effective viral inactivating agents. Methods for using ethyleneimine oligomers for inactivating viruses in biological compositions are described in U.S. Ser. No. 09/005,606 (filed Jan. 12, 1998), hereby incorporated by reference.

SUMMARY OF THE INVENTION

In general, the invention provides a method for synthesizing ethyleneimine dimer (1-aziridineethanamine) which includes reacting 2-(2-aminoethylamino)ethanol with an aqueous HX solution, where X is a halogen, to produce N-(2-haloethyl)-1,2-ethanediamine dihydrohalide, reacting the N-(2-haloethyl)-1,2-ethanediamine dihydrohalide with a base in a solvent to convert the N-(2-haloethyl)-1,2-ethanediamine dihydrohalide into ethyleneimine dimer, and then purifying the dimer from the solvent (e.g., by continuous extraction).

In preferred embodiments, the halogen is bromine (most preferred), chlorine, fluorine, or iodine. In another preferred embodiment, the HX is diluted, such that the solution is 30–55% (w/w) HX. In yet another preferred embodiment, the solvent includes a $C_{1-6}$ alcohol (e.g., ethanol or methanol) or water.

In other preferred embodiments, the HX is added dropwise to the 2-(2-aminoethylamino)ethanol, the temperature of the 2-(2-aminoethylamino)ethanol is less than 10° C. during the addition of the HX, and the reaction of 2-(2-aminoethyl amino)ethanol with HX includes the step of refluxing. Preferably, the yield of the N-(2-haloethyl)-1,2-ethanediamine dihydrohalide from this reaction is at least 50% of the theoretical yield. More preferably, the yield is at least 75% of the theoretical yield.

In still other preferred embodiments, reacting the N-(2-haloethyl)-1,2-ethanediamine dihydrohalide to produce ethyleneimine dimer includes the steps of refluxing and distillation. Preferably, the yield of ethyleneimine dimer from this reaction is at least 20% of the theoretical yield. More preferably, the yield is at least 25% of the theoretical yield, and most preferably, the yield is at least 30% of the theoretical yield.

Preferably, the ethyleneimine dimer which results from the method of synthesis is at least 90% pure, more preferably at least 95% pure, and most preferably at least 98% pure.

The method of synthesis described herein provides several advantages over previous methods: (1) The starting compounds are all relatively inexpensive; (2) the yield of product is greater than 20% of the theoretical yield; and (3) the steps of synthesis are easy, inexpensive and amenable to large-scale production. All of these advantages allow for less expensive production of ethyleneimine dimer.

Other features and advantages of the invention will be apparent from the following detailed description and from the claims.

DETAILED DESCRIPTION

An example of the synthesis is provided below. From the description provided herein, one skilled in the art can easily ascertain the essential characteristics of the present invention, and without departing from the spirit and scope thereof, can make various changes and modifications of the invention to adapt it to various usages and conditions.

EXAMPLE

Synthesis of Ethyleneimine Dimer

Step 1: Synthesis of N-(2-Bromoethyl)-1,2-Ethanediamine Dihydrobromide from 2-(2-Aminoethylamino)Ethanol N-(2-bromoethyl)-1,2-ethanediamine dihydrobromide is synthesized as follows. 100 mL of chilled (0.99 moles) of 2-(2-aminoethylamino)ethanol is placed in an ice bath for about 30–45 minutes. 1L (8.84 moles) of 48% (w/w) hydrobromic acid is added dropwise over 1.5 hours. This mixture is distilled in a vigreux distillation apparatus until the temperature distillate is 124° C. (three hours), refluxed for four hours, distilled to 124° C. (1.5 hours), refluxed for four hours, distilled to 124° C. (30 minutes), refluxed for four hours, distilled to 124° C. (30 minutes), refluxed for four hours, and distilled to 124° C. (10 minutes). The remainder of the HBr is removed when the mixture is cooled and concentrated on a rotary evaporator under vacuum at 6 mm pressure. The resulting residue is dissolved in boiling EtOH/H$_2$O (1175 mL/125 mL) and allowed to crystallize at 4° C. for about 12 hours. The crystals are collected by filtration, washed with cold ethanol, and then recrystallized from EtOH/H$_2$O as described above. The crystals are collected by filtration, washed with cold EtOH, and dried in an oven under vacuum at 6 mm pressure at 60° C. for 12 hours. The yield is approximately 254.4 g (78% of theoretical yield) of white solid with a melting point of 170–171° C. This white powder is N-(2-bromoethyl)-1,2-ethanediamine dihydrobromide. Thin layer chromatography shows trace of a more-polar impurity.

A higher percent yield of N-(2-bromoethyl)-1,2-ethanediamine dihydrobromide can be obtained by allowing the pot residue remaining after the final vigreux distillation to cool to 95° C., and then adding to this pot residue 100 mL of 100% ethanol. N-(2-bromoethyl)-1,2-ethanediamine dihydrobromide will crystallize overnight. The solid is collected and washed several times with ice cold 100% ethanol. This yield is approximately 87% of theoretical yield.

The amount of HBr can be reduced to approximately 4 moles for every 1 mole of 2-(2-aminoethylamino)ethanol, thus reducing the cost of synthesis.

Step 2: Synthesis of Ethyleneimine Dimer from N-(2-Bromoethyl)-1,2-Ethanediamine Dihydrobromide Ethyleneimine dimer is synthesized as follows. Sodium hydroxide (32.04 g) is dissolved in 50 mL deionized water and chilled in an ice bath to below 25° C. To this solution is added 65.78 g (0.2 moles) of N-(2-bromoethyl)-1,2-ethanediamine dihydrobromide and 250 mL ethanol. The reaction mixture is refluxed for about one hour. The reaction mixture is cooled, then distilled in a vigreux distillation apparatus under reduced pressure to remove the bulk of the ethanol. The pot residue is loaded into a continuous extractor and extracted with ether for 42 hours. The ether extract is dried over sodium sulfate, filtered, and then distilled through a vigreux column first under argon and then under reduced pressure. Fractions with a high percentage of dimer (as determined by gas chromatography) are further distilled two or more times (the final distillation from sodium) to give 5.2 g of a clear, colorless liquid, with a boiling point of 78–80° C. at 138 mm Hg. This liquid is 99.3% ethyleneimine dimer by gas chromatography, corresponding to a 30% yield (2.6% water by Karl Fischer water determination).

Ethyleneimine dimer can also be synthesized from N-(2-bromoethyl)1,2-ethanediamine dihydrobromide as follows. 1.152 kg of sodium hydroxide (28.8 moles) is placed into a 12 L three-neck round bottom flask. To this is added 5.85 L of HPLC-grade methanol. The reaction mixture is cooled for about two hours to 8° C. 2.367 kg (7.2 moles) of N-(2-bromoethyl)-1,2-ethanediamine dihydrobromide is then added to the reaction mixture over 15 minutes. The temperature should be about 9° C. at the end of the addition. The reaction mixture is refluxed for one hour, and then cooled to room temperature. The solid is removed by filtration, and the methanol is distilled from the filtrate under argon atmosphere. The distillate should be about 5.52 L. The pot residue is cooled to room temperature under argon and additional solid is removed by filtration. The filtrate is cooled in a 4° C. refrigerator for four hours, and newly formed solid is removed by filtration. The filtrate is distilled through a vigreux column under vacuum (138 mm Hg) and fractions are collected. Ethyleneimine content is determined using gas chromatography. Fractions with a high percentage of dimer (as determined by gas chromatography) are distilled to purity, as described above, resulting in 186 g of a clear, colorless liquid with a boiling point of 78–80° C. at 138 mm Hg. The yield is 30% of theoretical yield.

The purity of the synthesized ethyleneimine dimer is determined using standard methods of gas chromatography known to those skilled in the art. A suitable column is a RESTEK RTX®-5.15 m×0.53 mm×1.0 µm analytical column, compatible with, for example, a Hewlett Packard Model 6890 Series with FID detection. Using the method of synthesis described herein, the ethyleneimine dimer is at least 98% pure. Thin layer chromatography shows piperazine as an impurity.

What is claimed is:

1. A method of synthesizing ethyleneimine dimer, said method comprising the steps:
   (a) reacting 2-(2-aminoethylamino)ethanol with an aqueous HX solution, where X is a halogen, to produce N-(2-haloethyl)-1,2-ethanediamine dihydrohalide;
   (b) reacting said N-(2-haloethyl)-1,2-ethanediamine dihydrohalide with a base in a solvent to convert said N-(2-haloethyl)-1,2-ethanediamine dihydrohalide into ethyleneimine dimer; and
   (c) purifying said ethyleneimine dimer from said solvent.

2. The method of claim 1, wherein X is Br, Cl, I, or F.

3. The method of claim 2, wherein X is Br.

4. The method of claim 1, wherein said HX solution is 30–55% (w/w) HX.

5. The method of claim 1, wherein said solvent comprises water or a $C_{1-6}$ alcohol.

6. The method of claim 1, wherein said HX solution is added to said 2-(2-aminoethylamino)ethanol such that the temperature of the reaction mixture is less than 10° C. during said addition.

7. The method of claim 1, wherein said HX is added drop-wise to said 2-(2-aminoethylamino)ethanol.

8. The method of claim 1, wherein said reacting 2-(2-aminoethyl amino)ethanol with HX comprises the step of refluxing.

9. The method of claim 1, wherein the yield of said N-(2-haloethyl)-1,2-ethanediamine dihydrohalide from said 2-(2-aminoethylamino)ethanol is at least 50% of the theoretical yield.

10. The method of claim 1, wherein the yield of said N-(2-haloethyl)1,2-ethanediamine dihydrohalide from said 2-(2-aminoethylamino)ethanol is at least 75% of the theoretical yield.

11. The method of claim 5, wherein said reacting said N-(2-haloethyl)-1,2-ethanediamine dihydrohalide in said $C_{1-6}$ alcohol to produce ethyleneimine dimer comprises the step of refluxing.

12. The method of claim 1, wherein said reacting said N-(2-haloethyl)-1,2-ethanediamine dihydrohalide to produce ethyleneimine dimer comprises the step of distillation.

13. The method of claim 1, wherein said purifying comprises a continuous extraction.

14. The method of claim 1, wherein said purifying comprises a series of distillations and filtrations.

15. The method of claim 1, wherein said ethyleneimine dimer is at least 90% pure after said purifying step (c).

16. The method of claim 1, wherein said ethyleneimine dimer is at least 95% pure after said purifying step (c).

17. The method of claim 1, wherein said ethyleneimine dimer is at least 98% pure after said purifying step (c).

18. The method of claim 1, wherein the yield of said ethyleneimine dimer from said N-(2-haloethyl)-1,2-ethanediamine dihydrohalide is at least 20% of the theoretical yield.

19. The method of claim 1, wherein the yield of said ethyleneimine dimer from said N-(2-haloethyl)-1,2-ethanediamine dihydrohalide is at least 25% of the theoretical yield.

20. The method of claim 1, wherein the yield of said ethyleneimine dimer from said N-(2-haloethyl)-1,2-ethanediamine dihydrohalide is at least 30% of the theoretical yield.

21. A method of synthesizing ethyl ethyleneimine dimer, said method comprising the steps:
   (a) reacting 2-(2-aminoethylamino)ethanol with HBr to produce N-(2-bromoethyl)-1,2-ethanediamine dihydrobromide; and
   (b) reacting said N-(2-bromoethyl)-1,2-ethanediamine dihydrobromide with a base in a solvent having a pH>7.5 to convert said N-(2-bromoethyl)-1,2-ethanediamine dihydrobromide into ethyleneimine dimer.

* * * * *

UNITED STATES PATENT AND TRADEMARK OFFICE
CERTIFICATE OF CORRECTION

PATENT NO. : 6,215,003 B1
DATED : April 10, 2001
INVENTOR(S) : Kevin S. Plunkett Page 1 of 1

It is certified that error appears in the above-identified patent and that said Letters Patent is hereby corrected as shown below:

Column 2,
Line 31, replace "IL" with -- 1L --;

Column 3,
Line 45, replace "μm analytical column" with -- μm 5% diphenyl/95% dimethylpolysiloxane analytical column -- and;

Column 4, claim 21,
Line 51, delete the word "ethyl."

Signed and Sealed this

Sixteenth Day of April, 2002

Attest:

Attesting Officer

JAMES E. ROGAN
Director of the United States Patent and Trademark Office